(12) United States Patent
Hayzlett et al.

(10) Patent No.: US 10,722,339 B2
(45) Date of Patent: Jul. 28, 2020

(54) FLOWABLE TISSUE PRODUCTS

(71) Applicant: LifeCell Corporation, Branchburg, NJ (US)

(72) Inventors: Mark Hayzlett, Flemington, NJ (US); Ivis Munoz, East Stroudsburg, PA (US); Nimesh Kabaria, Somerset, NJ (US); Joshua Czeczuga, Hillsborough, NJ (US)

(73) Assignee: LifeCell Corporation, Madison, NJ (US)

( * ) Notice: Subject to any disclaimer, the term of this patent is extended or adjusted under 35 U.S.C. 154(b) by 107 days.

(21) Appl. No.: 15/883,335

(22) Filed: Jan. 30, 2018

(65) Prior Publication Data

US 2018/0153675 A1    Jun. 7, 2018

Related U.S. Application Data

(63) Continuation of application No. 15/377,481, filed on Dec. 13, 2016, now Pat. No. 9,913,705, which is a continuation of application No. 13/717,808, filed on Dec. 18, 2012, now Pat. No. 9,549,805.

(60) Provisional application No. 61/577,729, filed on Dec. 20, 2011.

(51) Int. Cl.
*A61F 2/02* (2006.01)
*A61L 27/36* (2006.01)

(52) U.S. Cl.
CPC .............. *A61F 2/02* (2013.01); *A61L 27/362* (2013.01); *A61L 27/3604* (2013.01); *A61L 27/3608* (2013.01); *A61L 27/3612* (2013.01); *A61L 27/3625* (2013.01); *A61L 27/3683* (2013.01); *A61L 27/3691* (2013.01); *A61L 2400/06* (2013.01); *A61L 2430/34* (2013.01); *A61L 2430/40* (2013.01)

(58) Field of Classification Search
CPC ........................................................ A61F 2/02
USPC ....... 623/8, 13.11–13.2, 14.12, 15.12, 23.51, 623/23.55, 23.61–23.63, 23.72, 23.75, 623/23.76; 424/422, 423, 426; 523/113–114
See application file for complete search history.

(56) References Cited

U.S. PATENT DOCUMENTS

| | | | |
|---|---|---|---|
| 4,347,841 A | 9/1982 | Benyo et al. |
| 4,350,629 A | 9/1982 | Yannas et al. |
| 4,352,883 A | 10/1982 | Lim |
| 4,582,640 A | 4/1986 | Smestad et al. |
| 4,776,173 A | 10/1988 | Kamarei et al. |

(Continued)

FOREIGN PATENT DOCUMENTS

| | | |
|---|---|---|
| CA | 1336812 C | 8/1995 |
| FR | 1522286 A | 4/1968 |

(Continued)

OTHER PUBLICATIONS

Ahn et al., The past, present, and future of xenotransplantation. Yonsei Med J. Dec. 31, 2004;45(6):1017-24.

(Continued)

*Primary Examiner* — Yashita Sharma
(74) *Attorney, Agent, or Firm* — McCarter & English, LLP

(57) ABSTRACT

The present disclosure provides tissue fillers. The tissue fillers can include a plurality of tissue particles formed from acellular tissue matrix fragments. The tissue fillers can be used to fill tissue sites, such as voids formed after tissue resection.

12 Claims, 1 Drawing Sheet

(56) References Cited

U.S. PATENT DOCUMENTS

| | | | |
|---|---|---|---|
| 4,796,603 A | 1/1989 | Dahlke et al. |
| 4,854,316 A | 8/1989 | Davis |
| 4,902,508 A | 2/1990 | Badylak et al. |
| 4,969,912 A | 11/1990 | Kelman et al. |
| 5,104,957 A | 4/1992 | Kelman et al. |
| 5,131,850 A | 7/1992 | Brockbank |
| 5,160,313 A | 11/1992 | Carpenter et al. |
| 5,231,169 A | 7/1993 | Constantz et al. |
| 5,254,133 A | 10/1993 | Seid |
| 5,256,140 A * | 10/1993 | Fallick ............... A61K 8/02 424/572 |
| 5,275,826 A | 1/1994 | Badylak et al. |
| 5,284,655 A | 2/1994 | Bogdansky et al. |
| 5,332,802 A | 7/1994 | Kelman et al. |
| 5,332,804 A | 7/1994 | Florkiewicz et al. |
| 5,336,616 A | 8/1994 | Livesey et al. |
| 5,364,756 A | 11/1994 | Livesey et al. |
| 5,439,684 A | 8/1995 | Prewett et al. |
| 5,489,304 A | 2/1996 | Orgill et al. |
| 5,613,982 A | 3/1997 | Goldstein |
| 5,632,778 A | 5/1997 | Goldstein |
| 5,634,931 A | 6/1997 | Kugel |
| 5,641,518 A | 6/1997 | Badylak et al. |
| 5,648,330 A | 7/1997 | Pierschbacher et al. |
| 5,695,998 A | 12/1997 | Badylak et al. |
| 5,712,252 A | 1/1998 | Smith |
| 5,728,752 A | 3/1998 | Scopelianos et al. |
| 5,739,176 A | 4/1998 | Dunn et al. |
| 5,780,295 A | 7/1998 | Livesey et al. |
| 5,800,537 A | 9/1998 | Bell |
| 5,893,888 A | 4/1999 | Bell |
| 5,942,496 A | 8/1999 | Bonadio et al. |
| 5,972,007 A | 10/1999 | Sheffield et al. |
| 5,993,844 A | 11/1999 | Abraham et al. |
| 6,027,743 A | 2/2000 | Khouri et al. |
| 6,096,347 A | 8/2000 | Geddes et al. |
| 6,113,623 A | 9/2000 | Sgro |
| 6,166,288 A | 12/2000 | Diamond et al. |
| 6,174,320 B1 | 1/2001 | Kugel et al. |
| 6,179,872 B1 | 1/2001 | Bell et al. |
| 6,194,136 B1 | 2/2001 | Livesey et al. |
| 6,197,036 B1 | 3/2001 | Tripp et al. |
| 6,231,608 B1 | 5/2001 | Stone |
| 6,258,125 B1 | 7/2001 | Paul et al. |
| 6,326,018 B1 | 12/2001 | Gertzman et al. |
| 6,371,992 B1 | 4/2002 | Tanagho et al. |
| 6,381,026 B1 | 4/2002 | Schiff et al. |
| 6,432,710 B1 | 8/2002 | Boss, Jr. et al. |
| 6,485,723 B1 | 11/2002 | Badylak et al. |
| 6,554,863 B2 | 4/2003 | Paul et al. |
| 6,576,265 B1 | 6/2003 | Spievack |
| 6,599,318 B1 | 7/2003 | Gabbay |
| 6,610,006 B1 | 8/2003 | Amid et al. |
| 6,638,284 B1 | 10/2003 | Rousseau et al. |
| 6,652,593 B2 | 11/2003 | Boyer, II et al. |
| 6,666,892 B2 | 12/2003 | Hiles et al. |
| 6,726,660 B2 | 4/2004 | Hessel et al. |
| 6,752,938 B2 | 6/2004 | Wang et al. |
| 6,767,369 B2 | 7/2004 | Boyer, II et al. |
| 6,776,800 B2 | 8/2004 | Boyer, II et al. |
| 6,790,213 B2 | 9/2004 | Cherok et al. |
| 6,833,408 B2 | 12/2004 | Sehl et al. |
| 6,933,326 B1 | 8/2005 | Griffey et al. |
| 7,105,001 B2 | 9/2006 | Mandelbaum |
| 7,235,295 B2 | 6/2007 | Laurencin et al. |
| 7,358,284 B2 * | 4/2008 | Griffey ............... A61K 9/0024 424/422 |
| 7,425,322 B2 | 9/2008 | Cohn et al. |
| 7,498,040 B2 | 3/2009 | Masinaei et al. |
| 7,498,041 B2 | 3/2009 | Masinaei et al. |
| 7,799,767 B2 | 9/2010 | Lamberti et al. |
| 7,815,561 B2 | 10/2010 | Forman et al. |
| 7,838,021 B2 | 11/2010 | Lafont et al. |
| 8,067,149 B2 | 11/2011 | Livesey et al. |
| 8,323,352 B2 | 12/2012 | Friedman et al. |
| 8,324,449 B2 | 12/2012 | McQuillan et al. |
| 8,333,803 B2 | 12/2012 | Park et al. |
| 8,652,500 B2 * | 2/2014 | Bosley, Jr. ............... A61L 27/26 424/422 |
| 9,549,805 B2 | 1/2017 | Hayzlett et al. |
| 9,913,705 B2 | 3/2018 | Hayzlett et al. |
| 2002/0055143 A1 | 5/2002 | Bell et al. |
| 2002/0061328 A1 | 5/2002 | Gertzman et al. |
| 2002/0082697 A1 | 6/2002 | Damien |
| 2002/0099344 A1 | 7/2002 | Hessel et al. |
| 2002/0103542 A1 | 8/2002 | Bilbo |
| 2002/0120347 A1 | 8/2002 | Boyer, II et al. |
| 2002/0197242 A1 | 12/2002 | Gertzman et al. |
| 2003/0009235 A1 | 1/2003 | Manrique et al. |
| 2003/0035843 A1 | 2/2003 | Livesey et al. |
| 2003/0039678 A1 | 2/2003 | Stone et al. |
| 2003/0143207 A1 | 7/2003 | Livesey et al. |
| 2004/0037735 A1 | 2/2004 | DePaula et al. |
| 2004/0059364 A1 | 3/2004 | Gaskins et al. |
| 2004/0078077 A1 | 4/2004 | Binette et al. |
| 2004/0078089 A1 | 4/2004 | Ellis et al. |
| 2005/0008672 A1 | 1/2005 | Winterbottom et al. |
| 2005/0009178 A1 | 1/2005 | Yost et al. |
| 2005/0028228 A1 | 2/2005 | McQuillan et al. |
| 2005/0043716 A1 | 2/2005 | Frimer |
| 2005/0054771 A1 | 3/2005 | Sehl et al. |
| 2005/0058629 A1 | 3/2005 | Harmon et al. |
| 2005/0118230 A1 | 6/2005 | Hill et al. |
| 2005/0159822 A1 | 7/2005 | Griffey et al. |
| 2005/0220848 A1 * | 10/2005 | Bates ............... A61F 2/06 424/443 |
| 2005/0288691 A1 | 12/2005 | Leiboff |
| 2006/0073592 A1 | 4/2006 | Sun et al. |
| 2006/0078591 A1 * | 4/2006 | Del Vecchio ............... A61B 17/322 424/426 |
| 2006/0105026 A1 | 5/2006 | Fortune et al. |
| 2006/0106419 A1 | 5/2006 | Gingras |
| 2006/0115515 A1 | 6/2006 | Pirhonen et al. |
| 2006/0210960 A1 | 9/2006 | Livesey et al. |
| 2006/0247206 A1 | 11/2006 | Feins |
| 2006/0276908 A1 | 12/2006 | Sogaard-Andersen et al. |
| 2007/0009586 A1 | 1/2007 | Cohen et al. |
| 2007/0078522 A2 | 4/2007 | Griffey et al. |
| 2007/0104759 A1 | 5/2007 | Dunn et al. |
| 2007/0111937 A1 | 5/2007 | Pickar et al. |
| 2007/0202173 A1 | 8/2007 | Cueto-Garcia |
| 2007/0248575 A1 | 10/2007 | Connor et al. |
| 2007/0293878 A1 | 12/2007 | Butsch |
| 2008/0027542 A1 | 1/2008 | McQuillan et al. |
| 2008/0027562 A1 | 1/2008 | Fujisato et al. |
| 2008/0033461 A1 | 2/2008 | Koeckerling et al. |
| 2008/0071300 A1 | 3/2008 | Popadiuk et al. |
| 2008/0091277 A1 | 4/2008 | Deusch et al. |
| 2008/0095819 A1 | 4/2008 | Gourdie et al. |
| 2008/0113035 A1 | 5/2008 | Hunter |
| 2008/0131509 A1 | 6/2008 | Hossainy et al. |
| 2008/0147199 A1 | 6/2008 | Yost et al. |
| 2008/0167729 A1 | 7/2008 | Nelson et al. |
| 2009/0035289 A1 | 2/2009 | Wagner et al. |
| 2009/0130221 A1 | 5/2009 | Bolland et al. |
| 2009/0306790 A1 | 12/2009 | Sun |
| 2010/0021961 A1 | 1/2010 | Fujisato et al. |
| 2010/0040687 A1 | 2/2010 | Pedrozo et al. |
| 2010/0209408 A1 | 8/2010 | Stephen A. et al. |
| 2010/0272782 A1 | 10/2010 | Owens et al. |
| 2011/0020271 A1 | 1/2011 | Niklason et al. |
| 2012/0010728 A1 | 1/2012 | Sun et al. |
| 2012/0040013 A1 | 2/2012 | Owens et al. |
| 2012/0263763 A1 | 10/2012 | Sun et al. |
| 2013/0053960 A1 | 2/2013 | Park et al. |
| 2013/0121970 A1 | 5/2013 | Owens et al. |
| 2013/0158676 A1 | 6/2013 | Hayzlett et al. |

FOREIGN PATENT DOCUMENTS

| | | |
|---|---|---|
| WO | WO-1984/04880 A1 | 12/1984 |
| WO | WO-1991/16867 A1 | 11/1991 |
| WO | WO-1994/03584 A1 | 2/1994 |
| WO | WO-1995/22301 A1 | 8/1995 |

(56) References Cited

FOREIGN PATENT DOCUMENTS

| | | |
|---|---|---|
| WO | WO-1996/13974 A1 | 5/1996 |
| WO | WO-1999/32049 A1 | 7/1999 |
| WO | WO-1999/47080 A1 | 9/1999 |
| WO | WO-1999/51170 A1 | 10/1999 |
| WO | WO-1999/63051 A2 | 12/1999 |
| WO | WO-1999/65470 A1 | 12/1999 |
| WO | WO-2000/16822 A1 | 3/2000 |
| WO | WO-2000/47114 A1 | 8/2000 |
| WO | WO-2003/017826 A2 | 3/2003 |
| WO | WO-2003/032735 A1 | 4/2003 |
| WO | WO-2005/009134 A1 | 2/2005 |
| WO | WO-2007/043513 A1 | 4/2007 |
| WO | WO-2007/134134 A2 | 11/2007 |
| WO | WO-2009/009620 A2 | 1/2009 |
| WO | WO-2010/019753 A2 | 2/2010 |
| WO | WO-2010/078353 A2 | 7/2010 |
| WO | WO-2012/142419 A1 | 10/2012 |
| WO | WO-2012/166784 A1 | 12/2012 |

OTHER PUBLICATIONS

Allman et al., Xenogeneic extracellular matrix grafts elicit a TH2-restricted immune response. Transplantation. Jun. 15, 2001;71(11):1631-40.

Aycock et al., Parastomal hernia repair with acellular dermal matrix. J Wound Ostomy Continence Nurs. Sep.-Oct. 2007;34(5):521-3.

Badylak et al., Endothelial cell adherence to small intestinal submucosa: an acellular bioscaffold. Biomaterials. Dec. 1999;20(23-24):2257-63.

Badylak et al., Extracellular matrix as a biological scaffold material: Structure and function. Acta Biomater. Jan. 2009;5(1):1-13.

Beniker et al., The use of acellular dermal matrix as a scaffold for periosteum replacement. Orthopedics. May 2003;26(5 Suppl):s591-6.

Bruder et al., The effect of implants loaded with autologous mesenchymal stem cells on the healing of canine segmental bone defects. J Bone Joint Surg Am. Jul. 1998;80(7):985-96.

Buma et al., Tissue engineering of the meniscus. Biomaterials. Apr. 2004;25(9):1523-32.

Chaplin et al., Use of an acellular dermal allograft for dural replacement: an experimental study. Neurosurgery. Aug. 1999;45(2):320-7.

Chen et al., Acellular collagen matrix as a possible "off the shelf" biomaterial for urethral repair. Urology. Sep. 1999;54(3):407-10.

Collins et al., Cardiac xenografts between primate species provide evidence for the importance of the alpha-galactosyl determinant in hyperacute rejection. J Immunol. May 15, 1995;154(10):5500-10.

Costantino et al., Human dural replacement with acellular dermis: clinical results and a review of the literature. Head Neck. Dec. 2000;22(8):765-71.

Dobrin et al., Elastase, collagenase, and the biaxial elastic properties of dog carotid artery. Am J Physiol. Jul. 1984;247(1 Pt 2):H124-31.

Edel, The use of a connective tissue graft for closure over an immediate implant covered with occlusive membrane. Clin Oral Implants Res. Mar. 1995;6(1):60-5.

Farso Nielsen et al., Biodegradable guide for bone regeneration. Polyurethane membranes tested in rabbit radius defects. Acta Orthop Scand. Feb. 1992;63(1):66-9.

Fowler et al., Ridge Preservation Utilizing an Acellular Dermal Allograft and Demineralized Freeze-Dried Bone Allograft: Part II. Immediate Endosseous Impact Placement. J Periodontol. Aug. 2000;71(8):1360-1364.

Fowler et al., Root coverage with an acellular dermal allograft: a three-month case report. J Contemp Dent Pract. Aug. 15, 2000;1(3):47-59.

Galili et al., Interaction between human natural anti-alpha-galactosyl immunoglobulin G and bacteria of the human flora. Infect Immun. Jul. 1988;56(7):1730-7.

Galili et al., Man, apes, and Old World monkeys differ from other mammals in the expression of alpha-galactosyl epitopes on nucleated cells. J Biol Chem. Nov. 25, 1988;263(33):17755-62.

Galili, Interaction of the natural anti-Gal antibody with alpha-galactosyl epitopes: a major obstacle for xenotransplantation in humans. Immunol Today. Oct. 1993;14(10):480-2.

Gamba et al., Experimental abdominal wall defect repaired with acellular matrix. Pediatr. Surg Int. Sep. 2002;18(5-6):327-31.

Gazdar et al., SV40 and human tumours: myth, association or casualty? Nature Reviews Cancer. Dec. 2002;2:957-964.

Gebhart et al., A radiographical and biomechanical study of demineralized bone matrix implanted into a bone defect of rat femurs with and without bone marrow. Acta Orthop Belg. 1991;57(2):130-43.

Gong et al., A sandwich model for engineering cartilage with acellular cartilage sheets and chondrocytes. Biomaterials. Mar. 2011;32(9):2265-73.

Good et al., Identification of carbohydrate structures that bind human antiporcine antibodies: implications for discordant xenografting in humans. Transplant Proc. Apr. 1992;24(2):559-62.

Greenstein et al., Parastomal hernia repair using cross-linked porcine dermis: report of a case. Surg Today. 2008;38(11):1048-51.

Griffey et al., Particulate dermal matrix as an injectable soft tissue replacement material. J Biomed Mater Res. 2001;58(1):10-5.

Hamadeh et al., Human natural anti-Gal IgG regulates alternative complement pathway activation on bacterial surfaces. J Clin Invest. Apr. 1992;89(4):1223-35.

Hammond et al., Human in vivo cellular response to a cross-linked acellular collagen implant. Br J Surg. Apr. 2008;95(4):438-46.

Hammond et al., Parastomal hernia prevention using a novel collagen implant: a randomised controlled phase 1 study. Hernia. Oct. 2008;12(5):475-81.

Harris, A comparative study of root coverage obtained with an acellular dermal matrix versus a connective tissue graft: results of 107 recession defects in 50 consecutively treated patients. Int J Periodontics Restorative Dent. Feb. 2000;20(1):51-9.

Harris, Root coverage with a connective tissue with partial thickness double pedicle graft and an acellular dermal matrix graft: a clinical and histological evaluation of a case report. J Periodontol. Nov. 1998;69(11):1305-11.

Hildebrand et al., Response of donor and recipient cells after transplantation of cells to the ligament and tendon. Microsc Res Tech. Jul. 1, 2002;58(1):34-8.

Inan et al., Laparoscopic repair of parastomal hernia using a porcine dermal collagen (Permacol) implant. Dis Colon Rectum. Sep. 2007;50(9):1465.

Karlinsky et al., In vitro effects of elastase and collagenase on mechanical properties of hamster lungs. Chest. Feb. 1976;69(2 Suppl):275-6.

Kay et al., Guided bone regeneration: integration of a resorbable membrane and a bone graft material. Pract Periodontics Aesthet Dent. Mar. 1997;9(2):185-94.

Kilpadi et al., Evaluation of closed incision management with negative pressure wound therapy (CIM): hematoma/seroma and involvement of the lymphatic system. Wound Repair Regen. Sep.-Oct. 2011;19(5):588-96.

Kish et al., Acellular dermal matrix (AlloDerm): new material in the repair of stoma site hernias. Am Surg. Dec. 2005;71(12):1 047-50.

Kridel et al., Septal perforation repair with acellular human dermal allograft. Arch Otolaryngol Head Neck Surg. Jan. 1998;124(1):73-8.

Laidlaw et al., Tympanic membrane repair with a dermal allograft. Laryngoscope. Apr. 2001;111(4 Pt 1):702-7.

Lee et al., In vitro evaluation of a poly(lactide-co-glycolide)-collagen composite scaffold for bone regeneration. Biomaterials. Jun. 2006;27(18):3466-72.

Lu et al., Novel porous aortic elastin and collagen scaffolds for tissue engineering. Biomaterials. Oct. 2004;25(22):5227-37.

Lynn et al., Antigenicity and immunogenicity of collagen. J Biomed Mater Res B Appl Biomater. Nov. 15, 2004;71(2):343-54.

Mantovani et al., Reconstructive urethroplasty using porcine acellular matrix: preliminary results. Arch Ital Urol Androl. Sep. 2002;74(3):127-8.

(56) References Cited

OTHER PUBLICATIONS

Marzaro et al., Autologous satellite cell seeding improves in vivo biocompatibility of homologous muscle acellular matrix implants. Int J Mol Med. Aug. 2002;10(2):177-82.

Merguerian et al., Acellular bladder matrix allografts in the regeneration of functional bladders: evaluation of large-segment (> 24 cm) substitution in a porcine model. BJU Int. May 2000;85(7):894-8.

Novaes et al., Acellular dermal matrix graft as a membrane for guided bone regeneration: a case report. Implant Dent. 2001;10(3):192-6.

Omae et al., Multilayer tendon slices seeded with bone marrow stromal cells: a novel composite for tendon engineering. J Orthop Res. Jul. 2009;27(7):937-42.

Parnigotto et al., Experimental defect in rabbit urethra repaired with acellular aortic matrix. Urol Res. Jan. 2000;28(1):46-51.

Pluchino et al., Neural stem cells and their use as therapeutic tool in neurological disorders. Brain Res Brain Res Rev. Apr. 2005;48(2):211-9.

Qui et al., Evaluation of bone regeneration at critical-sized calvarial defect by DBM/AM composite. J Biomed Mater Res B Appl Biomater. May 2007;81(2):516-23.

Rabie et al., Integration of endochondral bone grafts in the presence of demineralized bone matrix. Int J Oral Maxillofac Surg. Aug. 1996;25(4):311-8.

Reddy et al., Regeneration of functional bladder substitutes using large segment acellular matrix allografts in a porcine model. J Urol. Sep. 2000;164(3 Pt 2):936-41.

Reihsner et al., Biomechanical properties of elastase treated palmar aponeuroses. Connect Tissue Res. 1991;26(1-2):77-86.

Ruszczak, Effect of collagen matrices on dermal wound healing. Adv Drug Deliv Rev. Nov. 28, 2003;55(12):1595-611.

Sandor et al., Host response to implanted porcine-derived biologic materials in a primate model of abdominal wall repair. Tissue Eng Part A. Dec. 2008;14(12):2021-31.

Sandrin et al., Anti-pig IgM antibodies in human serum react predominantly with Gal(alpha 1-3)Gal epitopes. Proc Natl Acad Sci U S A. Dec. 1, 1993;90(23):11391-5.

Seandel et al., Growth factor-induced angiogenesis in vivo requires specific cleavage of fibrillar type I collagen. Blood. Apr. 15, 2001;97(8):2323-32.

Simon et al., Early failure of the tissue engineered porcine heart valve SYNERGRAFT in pediatric patients. Eur J Cardiothorac Surg. Jun. 2003;23(6):1002-6.

Sodian et al., Early in vivo experience with tissue-engineered trileaflet heart valves. Circulation. Nov. 7, 2000;102(19 Suppl 3):III22-9.

Stanworth et al., Stem cells: progress in research and edging towards the clinical setting. Clin Med (Lond). Sep.-Oct. 2001;1(5):378-82.

Suckow et al., Enhanced bone regeneration using porcine small intestinal submucosa. J Invest Surg. Sep.-Oct. 1999;12(5):277-87.

Tauro et al., Comparison of bovine collagen xenografts to autografts in the rabbit. Clin Orthop Relat Res. May 1991;(266):271-84.

Tedder et al., Stabilized collagen scaffolds for heart valve tissue engineering. Tissue Eng Part A. Jun. 2009;15(6):1257-68.

Van Nooten et al., Acellular porcine and kangaroo aortic valve scaffolds show more intense immune-mediated calcification than cross-linked Toronto SPV valves in the sheep model. Interact Cardiovasc Thorac Surg. Oct. 2006;5(5):544-9.

Vunjak-Novakovic et al., Tissue engineering of ligaments. Annu Rev Biomed Eng. 2004;6:131-56.

Wagshall et al., Acellular dermal matrix allograft in the treatment of mucogingival defects in children: illustrative case report. ASDC J Dent Child. Jan.-Apr. 2002;69(1):39-43.

Warren et al., Dural repair using acellular human dermis: experience with 200 cases: technique assessment. Neurosurgery. Jun. 2000;46(6):1391-6.

Wefer et al., Homologous acellular matrix graft for vaginal repair in rats: a pilot study for a new reconstructive approach. World J Urol. Sep. 2002;20(4):260-3.

Wright Medical Technology, Comparative Analysis: GraftJacket™ Periosteum Replacement Scaffold & Sis™ Porcine Small Intestinal Submucosa. Medical Brochure. 5 pages. 2002.

Wright Medical Technology, Comparative Analysis: GraftJacket™ Periosteum Replacement Scaffold vs. Fascia Lata. Medical Brochure. 7 pages. 2002.

Wright Medical Technology, GraftJacket™ Acellular Periosteum Replacement Scaffold: An Ideal Template for Rapid Revascularization and Cellular Repopulation. Technical Monograph, SK 836-602. 11 pages. 2002.

Wright Medical Technology, Preliminary Pre-Clinical Studies on GraftJacket™ Acellular Periosteum Replacement Scaffold. Medical Brochure, SK 898-802. 10 pages. 2002.

Xu et al., A porcine-derived acellular dermal scaffold that supports soft tissue regeneration: removal of terminal galactose-alpha-(1,3)-galactose and retention of matrix structure. Tissue Eng Part A. Jul. 2009;15(7):1807-19.

Yuan et al., Effects of collagenase and elastase on the mechanical properties of lung tissue strips. J Appl Physiol (1985). Jul. 2000;89(1):3-14.

Zhao et al., the study of the feasibility of segmental bone defect repair with tissue-engineered bone membrane: a qualitative observation. Strategies Trauma Limb Reconstr. Sep. 2008;3(2):57-64.

Zheng et al., Porcine small intestine submucosa (SIS) is not an acellular collagenous matrix and contains porcine Dna: possible implications in human implantation. J Biomed Mater Res B Appl Biomater. Apr. 2005;73(1):61-7.

International Search Report and Written Opinion for Application No. PCT/US2009/046193, dated Jul. 30, 2010. 12 pages.

International Search Report and Written Opinion for Application No. PCT/US2009/065087, dated Aug. 3, 2010. 8 pages.

International Search Report and Written Opinion for Application No. PCT/US2011/047041, dated Oct. 25, 2011. 11 pages.

International Search Report and Written Opinion for Application No. PCT/US2012/064103, dated Feb. 1, 2013. 12 pages.

International Search Report and Written Opinion for Application No. PCT/US2012/070246, dated Feb. 22, 2013. 11 pages.

International Search Report and Written Opinion for Application No. PCT/US2012/070250, dated Feb. 22, 2013. 12 pages.

International Search Report and Written Opinion for Application No. PCT/US2013/021909, dated May 29, 2013. 6 pages.

International Search Report for Application No. PCT/US1999/013861, dated Oct. 18, 1999. 4 pages.

International Search Report for Application No. PCT/US2002/033456, dated Feb. 20, 2003. 3 pages.

U.S. Appl. No. 09/762,174, filed Nov. 22, 2000, by Griffey et al.: Ex Parte Quayle Action, dated Aug. 11, 2004.

U.S. Appl. No. 09/762,174, filed Nov. 22, 2000, by Griffey et al.: Final Office Action, dated Aug. 21, 2002.

U.S. Appl. No. 09/762,174, filed Nov. 22, 2000, by Griffey et al.: Non-Final Office Action, dated Dec. 30, 2003.

U.S. Appl. No. 09/762,174, filed Nov. 22, 2000, by Griffey et al.: Non-Final Office Action, dated Jan. 18, 2002.

U.S. Appl. No. 09/762,174, filed Nov. 22, 2000, by Griffey et al.: Notice of Allowance, dated Jan. 6, 2005.

U.S. Appl. No. 10/273,780, filed Oct. 18, 2002, by Livesey et al.: Appeal Brief, dated Nov. 3, 2010.

U.S. Appl. No. 10/273,780, filed Oct. 18, 2002, by Livesey et al.: Examiner's Answer to Appeal Brief, dated Jan. 26, 2011.

U.S. Appl. No. 10/273,780, filed Oct. 18, 2002, by Livesey et al.: Final Office Action, dated Jul. 6, 2009.

U.S. Appl. No. 10/273,780, filed Oct. 18, 2002, by Livesey et al.: Final Office Action, dated Jun. 3, 2010.

U.S. Appl. No. 10/273,780, filed Oct. 18, 2002, by Livesey et al.: Final Office Action, dated Mar. 26, 2007.

U.S. Appl. No. 10/273,780, filed Oct. 18, 2002, by Livesey et al.: Non-Final Office Action, dated Dec. 24, 2009.

U.S. Appl. No. 10/273,780, filed Oct. 18, 2002, by Livesey et al.: Non-Final Office Action, dated Dec. 7, 2012.

(56) References Cited

OTHER PUBLICATIONS

U.S. Appl. No. 10/273,780, filed Oct. 18, 2002, by Livesey et al.: Non-Final Office Action, dated Jun. 12, 2006.
U.S. Appl. No. 10/273,780, filed Oct. 18, 2002, by Livesey et al.: Non-Final Office Action, dated May 29, 2008.
U.S. Appl. No. 10/273,780, filed Oct. 18, 2002, by Livesey et al.: Non-Final Office Action, dated Oct. 21, 2005.
U.S. Appl. No. 10/273,780, filed Oct. 18, 2002, by Livesey et al.: Patent Board of Appeals Decision, dated Sep. 17, 2012.
U.S. Appl. No. 11/040,127, filed Jan. 20, 2005, by Griffey et al.: Non-Final Office Action, dated Apr. 10, 2007.
U.S. Appl. No. 11/040,127, filed Jan. 20, 2005, by Griffey et al.: Non-Final Office Action, dated Oct. 13, 2006.
U.S. Appl. No. 11/040,127, filed Jan. 20, 2005, by Griffey et al.: Notice of Allowance, dated Nov. 21, 2007.
U.S. Appl. No. 12/621,786, filed Nov. 19, 2009, by Friedman et al.: Notice of Allowance, dated Aug. 2, 2012.
U.S. Appl. No. 12/716,828, filed Mar. 3, 2010, by Livesey et al.: Non-Final Office Action, dated Apr. 26, 2013.
U.S. Appl. No. 12/716,828, filed Mar. 3, 2010, by Livesey et al.: Non-Final Office Action, dated Jun. 14, 2010.
U.S. Appl. No. 12/716,828, filed Mar. 3, 2010, by Livesey et al.: Non-Final Office Action, dated Nov. 10, 2010.
U.S. Appl. No. 13/415,355, filed Mar. 8, 2012, by Sun et al.: Final Office Action, dated Feb. 27, 2013.
U.S. Appl. No. 13/415,355, filed Mar. 8, 2012, by Sun et al.: Non-Final Office Action, dated Aug. 29, 2012.
U.S. Appl. No. 13/717,828, filed Dec. 18, 2012, by Hayzlett.
U.S. Appl. No. 13/743,962, filed Jan. 17, 2013, by Roock et al.
U.S. Appl. No. 13/868,588, filed Apr. 23, 2013, by Hayzlett.
Written Opinion issued in International Patent Application PCT/US99/13861, dated May 10, 2000 (5 pages).

* cited by examiner

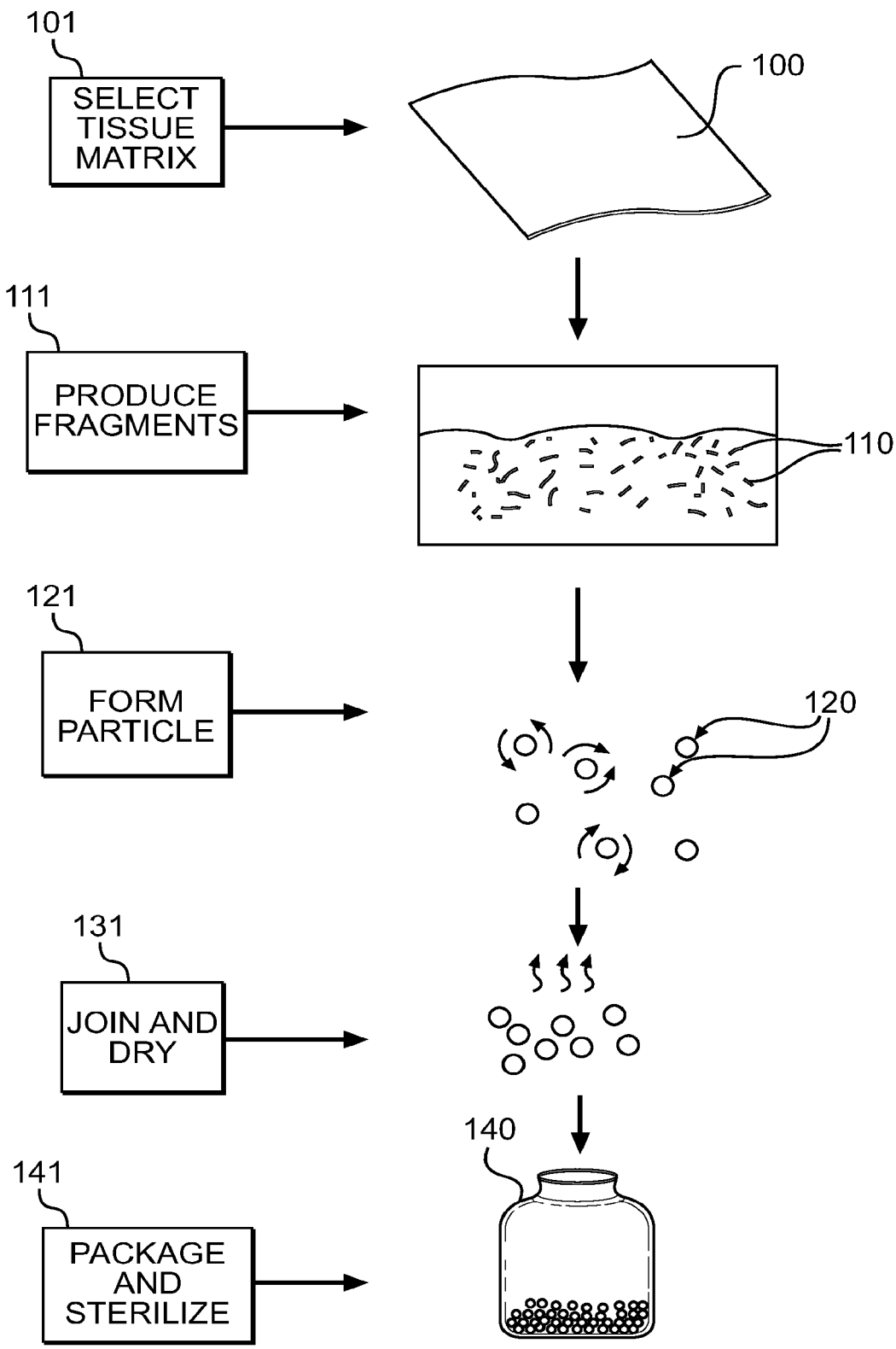

FLOWABLE TISSUE PRODUCTS

This application is a continuation of U.S. application Ser. No. 15/377,481, filed Dec. 13, 2016, which is a continuation of U.S. application Ser. No. 13/717,808, granted as U.S. Pat. No. 9,549,805 filed Dec. 18, 2012, which claims priority under 35 U.S.C. § 119 to U.S. Provisional Application No. 61/577,729, which was filed on Dec. 20, 2011.

The present disclosure relates to tissue products, and more particularly, particulate tissue products for use as tissue fillers.

Various tissue products have been produced to replace, augment, or treat tissue defects. For example, to replace or augment soft tissue defects, particulate acellular dermal matrices that form a paste or putty-like material can be used. Such products include, for example, CYMETRA®, which is a dermal acellular tissue matrix made by LIFECELL® Corporation (Branchburg, N.J.).

Although suitable for certain applications, further improvements in the ability of tissue products for soft or hard tissue treatment are desirable. The present disclosure describes improved tissue products produced from particulate tissue matrices.

SUMMARY

According to certain embodiments, a tissue product is provided. The product can include a plurality of dry tissue matrix particles comprising a longest dimension between about 1 mm and 5 mm. The tissue matrix particles can each comprise a plurality of tissue matrix fragments having a length between about 5 µm and 300 µm, wherein the tissue matrix fragments are formed into the tissue matrix particles.

According to certain embodiments, a method for producing a tissue treatment composition is provided. The method can include selecting a tissue matrix and treating the tissue matrix to produce fragments having a length between about 5 µm and 300 µm. The method can further include forming the fragments into a plurality of particles having a longest dimension between about 1 mm and about 5 mm; and treating the particles to join the fragments forming each particle to one another. In some embodiments, the present disclosure includes tissue products produced according to the disclosed methods.

According to certain embodiments, a method of treating a tissue site is provided. The method can comprise selecting a tissue site and selecting a tissue product, comprising a plurality of dry tissue particles, wherein the tissue matrix particles each comprise a plurality of tissue matrix fragments having a length between about 5 µm and 300 µm, and wherein the tissue matrix fragments are joined to one another to form the tissue matrix particles. The method can further comprise placing the plurality of tissue particles in or on the tissue site.

According to certain embodiments, a tissue product is provided. The tissue product can include plurality of dry tissue matrix particles that form a flowable mass that can be poured into a tissue site and will flow to fill and conform to a tissue site. The particles are substantially spherical and have a radius between about 1 mm and 5 mm. The tissue matrix particles each comprise a plurality of tissue matrix fragments having a length between about 5 µm and 300 µm, and the fragments are joined to one another to form the tissue matrix particles.

DESCRIPTION OF THE DRAWINGS

FIG. 1 illustrates a process for producing a tissue product according to various embodiments.

DESCRIPTION OF CERTAIN EXEMPLARY EMBODIMENTS

Reference will now be made in detail to certain exemplary embodiments according to the present disclosure, certain examples of which are illustrated in the accompanying drawings. Wherever possible, the same reference numbers will be used throughout the drawings to refer to the same or like parts.

In this application, the use of the singular includes the plural unless specifically stated otherwise. In this application, the use of "or" means "and/or" unless stated otherwise. Furthermore, the use of the term "including", as well as other forms, such as "includes" and "included", is not limiting. Any range described herein will be understood to include the endpoints and all values between the endpoints.

The section headings used herein are for organizational purposes only and are not to be construed as limiting the subject matter described. All documents, or portions of documents, cited in this application, including but not limited to patents, patent applications, articles, books, and treatises, are hereby expressly incorporated by reference in their entirety for any purpose.

As used herein "tissue product" will refer to any human or animal tissue that contains extracellular matrix proteins. "Tissue products" can include intact tissue matrices, acellular or partially decellularized tissue matrices, decellularized tissue matrices that have been repopulated with exogenous cells, and/or cellular tissues that have been processed to change the orientation of at least some of the collagen fibers within the tissue's extracellular matrix.

Various tissue products are available for treatment of hard and soft tissues. Such tissue products can include processed tissues, which have been treated to remove some or all of the cellular components and/or other materials (e.g., antigens and lipids). Such tissue products can be used for treatment, repair, regeneration, and/or augmentation of a variety of different tissues. For example, acellular tissue matrices can be used to replace soft tissue lost or damaged due to, for example, surgery, trauma, disease, and/or atrophy.

Current tissue matrices or other tissue scaffold or replacements materials (e.g., processed collagen or synthetic materials) are available in a variety of different forms. For example, STRATTICE™ and ALLODERM® (LIFECELL® Corporation, Branchburg, N.J.) are two acellular dermal tissue matrix products that are sold as sheets. In addition, CYMETRA® (also from LIFECELL®) is a dry, particulate acellular dermal matrix, which is produced by cryofracturing acellular dermis. Each of these materials can be used to treat various anatomic sites. STRATTICE™ and ALLODERM® can be used for soft tissue augmentation, e.g., to treat abdominal wall defects; and CYMETRA® can be injected for soft tissue augmentation.

Although some currently available tissue matrices are suitable for treatment of certain anatomic sites, such materials may not be well suited for some applications. For example, when treating tissue defects of varying size and geometry, e.g., after surgical excision of diseased tissue, sheets may not be well suited to allow complete filling of a tissue site. In addition, particulate materials may be packed or placed into a tissue site (e.g., in the form of a paste or putty), but such materials may not flow adequately to fill small defects, and may not maintain sufficient porosity or space for rapid cellular infiltration and formation of vascular structures. Accordingly, the present disclosure provides tissue products that can be used to fill tissue defects having variable and/or irregular geometries. In addition, the tissue products of the present disclosure can provide suitable configurations to allow cellular ingrowth and vascular formation.

In various embodiments, a tissue product is provided. The tissue product can include a plurality of dry tissue matrix particles. The particles can be formed from tissue fragments that are joined to one another to produce the desired particle size and shape. In various embodiments, the particles comprise a longest dimension between about 1 mm and 5 mm and the tissue matrix fragments that form the particles comprise a length between about 5 µm and 300 µm.

In various embodiments, a method for producing a tissue treatment composition is provided. The method can include selecting a tissue matrix and treating the tissue matrix to produce fragments having a length between about 5 µm and 300 µm. The method can further comprise forming the fragments into a plurality of particles having a longest dimension between about 1 mm and about 5 mm.

In various embodiments, methods for treating a tissue site are provided. The methods can comprise selecting a tissue site and selecting a tissue product comprising a plurality of dry tissue particles, wherein the tissue matrix particles each comprise a plurality of tissue matrix fragments having a length between about 5 µm and 300 µm, and wherein the tissue matrix fragments are joined to one another to form the tissue matrix particles; and placing the plurality of tissue particles in or on the tissue site.

In various embodiments a tissue product is provided. The tissue product can comprise a plurality of dry tissue matrix particles that form a flowable mass that can be poured into a tissue site and will flow to fill and conform to the tissue site. The particles are substantially spherical and have a radius between about 1 mm and 5 mm. The tissue matrix particles each comprise a plurality of tissue matrix fragments having a length between about 5 µm and 300 µm, wherein the tissue matrix fragments are joined to one another to form the tissue matrix particles.

In certain embodiments, the tissue products produced as described herein provide improved properties when implanted or during storage. For example, the products described herein may be less susceptible to damage caused during freezing than other acellular tissue matrices. In addition, the matrices may have an improved ability to allow cellular ingrowth and vascularization.

FIG. 1 illustrates a process for producing a tissue product according to various embodiments. As shown at step 101, the process begins with selecting a tissue matrix 100. Suitable tissue matrices are discussed further below, but the tissue matrices can include any substantially acellular tissue matrix produced from human or animal tissue, which retains the ability to support cellular ingrowth and tissue regeneration without excessive inflammation. Certain exemplary tissue matrices that may be used include STRATTICE™ and ALLODERM® (LIFECELL® Corporation, Branchburg, N.J.), which are porcine and human acellular dermal matrices, respectively. However, other suitable tissue matrices can be used, including, for example, small-intestine submucosa. In addition, the tissue matrices can include intact tissues (not decellularized) and/or tissues that have been partially decellularized and/or populated with exogenous cells.

Next, as shown at step 111, the matrix 100 is processed to produce fragments 110. The tissue fragments 110 can be formed using a range of sizes and different morphologies. For example, in some embodiments, the tissue fragments 110 are in the form of small strands or threads of tissue matrix that has been treated to produce the desired size distribution and/or shape. In various embodiments, the strands or threads have a length between about 5 µm and 300 µm, between about 50 µm and 200 µm, between about 50 µm and 300 µm, or any values in between. In certain embodiments, the strands are approximately 40 microns×140 microns to 100 microns by 350 microns.

The tissue fragments 110 can be produced using a variety of processes. For example, any suitable cutting, grinding, milling, blending, shearing, or other mechanical process can be used, which produces the desired size and shape and does not cause unsuitable damage or change to the tissue matrix. In certain embodiments, the tissue fragments 110 are processed using a mill such as a SYMPAK® food mill or a QUADRO Attrition Mill (Quadro, Canada). In some embodiments, the tissue matrix 100 is cut into small pieces (e.g., 4 cm×4 cm) and then milled. In addition, the matrix may be blended briefly in a solution (e.g., PBS) prior to milling.

In some cases, the tissue matrices 100 can be processed to produce the fragments 110 when wet or submerged in a liquid. For example, the tissue matrices 100 can be milled or otherwise processed when submerged in a buffer such as PBS or any other suitable buffer. Further, after processing, the buffer can be at least partially removed by centrifuging or filtering to remove some or all of the liquid component. For example, a suitable centrifugation protocol can include centrifuging at 4,500 rpms for about 60 min.

After processing to produce tissue fragments 110, groups of the fragments 120 are formed to produce particles 120 having a desired shape, as shown at Step 121. The specific shapes and sizes of the particles 120 can vary based on the intended implantation site, to control space between particles to provide channels for cellular and vascular ingrowth, or to control the ability of the particles to flow into a desired treatment site. The tissue particles 120 can be shaped using a variety of molding or shaping processes. For example, the fragments 110 may be placed into a mold and/or compressed, rolled into a desired shape, or otherwise manually manipulated to produce the desired shape.

In some embodiments, the particles can be formed by immersion in a cold liquid. For example, fragments containing a buffer such as PBS can be extruded from a syringe and slowly dropped into liquid nitrogen. The material, when dropped into liquid nitrogen will form small particles, and the relative dimensions of the particles can be controlled by controlling the speed of extrusion and water content of the materials.

In some cases, after extrusion, the materials can be further processed to produce a desired shape and/or structure. For example, in some cases, the frozen materials are placed into a mixing device, such as a panner. A panner is a cooking attachment to a mixer, which acts like a rock tumbler or cement mixer; it rotates at a given speed and tumbles whatever objects are inside to achieve a coating of whatever powder or liquid is added. However, other similar mixing devices can be used. After placement in the mixing device, additional dry strands produced as discussed above may be added to the mixing device (e.g., at approximately a 1:1 ratio of particles and dry strands). The materials, with or without the additional dry strands can be processed in the panner or similar mixing device to produce a more spherical shape, and or change the size of the particles]. Optionally, the particles may be at least partially dried while in the panner. For example, the frozen particles in the mixing device can be exposed to low levels of hot air (e.g., approximately 48° C. as a velocity that does not blow the particles out of the processing device). As the particles in the mixing device are slowly heated and dried, additional tissue fragments in the form of dry powder may be added to keep the particles coated. Adding the dry powder, in this way, can assist in pulling residual moisture to the surface of the particles to dry the interior. Optionally, the particles may be further dried within the mixing device to remove most moisture.

A variety of shapes can be used for the tissue particles 120. For example, the tissue particles 120 can be formed into substantially spherical shapes, oblong shapes (e.g., ovoid), cubes, rectangles, noodles, pyramids, or any other desired shape. In some embodiments, the shape is selected to control flowability when implanted. For example, spherical shapes may be selected to allow a high degree of flowability. Alternatively, more oblong shapes may be selected to allow filling of a space while preventing migration out of a desired location. In addition, the specific shape may be selected to control the space between particles. For example, a spherical shape and size may be selected to produce a certain amount of porosity to allow cellular ingrowth and/or formation of vascular or extracellular structures.

In addition, the size of the particles can be varied based on a desired application. For example, the particles may have a longest dimension between about 1 mm and about 5 mm. Therefore, if the particles are spherical, the particles will have a diameter between about 1 mm and 5 mm, and if the particles are ovoid, the particles will have a long axis with a length between about 1 mm and 5 mm.

In various embodiments, the particles are processed such that the fragments making up the particles are joined to one another to form stable structures, as shown at Step 131. In certain embodiments, the fragments are joined without the use of substantial amounts of binder or adhesives. In addition in some embodiments, the fragments are dried using a process that is believed to join the fragments without significant cross-linking. For example, in some cases, the fragments may have frayed ends that interlock with one another. Further, in some embodiments, the fragments may bind to one another by non-covalent binding. As discussed elsewhere, the particles may be dried using a process such as convective drying, and such processes can produce particles having fragments that are joined to one another.

In some embodiments, the fragments are joined to one another by cross-linking. Cross-linking can be accomplished using a number of processes such as dehydrothermal cross-linking, exposure to UV light, and/or chemical cross-linking. In some embodiments, a dehydrothermal cross-linking process is used to allow cross-linking while simultaneously drying the particles. In addition, using any of the cross-linking processes, the particles may be further dried (e.g., by freeze-drying or air drying) to remove additional moisture.

In various embodiments, the tissue products can be selected to have certain properties that facilitate implantation and tissue filling and/or regeneration. For example, in certain embodiments, the tissue particles are dry before implantation. The dry particles can form a flowable mass that will fill a void or pocket in a tissue site. The tissue particles can be dried by freeze-drying and/or concurrently with a dehydrothermal cross-linking process. In addition, in the particles can be selected such that they swell when contacted with an aqueous environment, as may be present in a tissue site. As such, the particles can expand when implanted to fill a selected tissue site.

In some embodiments, the particles are dried by convective heating. For example, frozen particles may be placed in a convection dryer (e.g., HARVEST Brand Kitchen Convection Dryer). Drying may be performed at approximately 45° C. However, lower or higher temperatures may be used, as long as temperatures that cause unacceptable denaturation or other tissue damage are not used. In addition, it should be noted, that even when partially or mostly dried, as described above using a panner, the particles may be further dried to remove excess moisture.

After drying, the particles are packaged and sterilized to form a final product 140, as shown at Step 141. The product can be package in a variety of known medical containers and can be sterilized using conventional processes as long as the processes do not damage the product (e.g., by excessive cross-linking) in an unacceptable manner. In some embodiments, the product can be packaged in foil-to-foil pouches and irradiated. In some embodiments, the product can be irradiated with e-beam radiation. Suitable e-beam doses can include 15-22 kGy or ranges therebetween.

The tissue products of the present disclosure can be used to treat a variety of different soft tissue or hard tissue sites. For example, the products can be used to replace, repair, regenerate or augment tissue lost or destroyed due to surgery, trauma, and/or any pathologic process. In some embodiments, the tissue products can be implanted in a soft tissue site such as a lumpectomy site. In other embodiments, the products can be used to treat or augment bone, muscle, subcutaneous tissue, and/or adipose tissue.

In certain embodiments, internal negative pressure can be applied within the tissue product. In certain embodiments, negative pressure can serve to draw cells from surrounding tissue into the implanted acellular tissue product, increasing the rate at which native cells migrate into the tissue product and enhancing the speed and/or overall effectiveness of tissue approximation.

In certain exemplary embodiments, internal negative pressure is delivered to the acellular tissue matrix by a reduced pressure therapy device. The reduced pressure therapy device can include a pump fluidly connected, e.g., through a fluid passage or tubing to the acellular tissue matrix, and which delivers reduced or negative pressure to the acellular tissue matrix. A variety of reduced pressure therapy devices can be used. For example, suitable reduced pressure therapy devices include V.A.C.® therapy devices produced by KCI (San Antonio, Tex.).

Acellular Tissue Matrices

The term "acellular tissue matrix," as used herein, refers generally to any tissue matrix that is substantially free of cells and/or cellular components. Skin, parts of skin (e.g., dermis), and other tissues such as blood vessels, heart valves, fascia, cartilage, bone, and nerve connective tissue may be used to create acellular matrices within the scope of the present disclosure. Acellular tissue matrices can be tested or evaluated to determine if they are substantially free of cell and/or cellular components in a number of ways. For example, processed tissues can be inspected with light microscopy to determine if cells (live or dead) and/or cellular components remain. In addition, certain assays can be used to identify the presence of cells or cellular components. For example, DNA or other nucleic acid assays can be used to quantify remaining nuclear materials within the tissue matrices. Generally, the absence of remaining DNA or other nucleic acids will be indicative of complete decellularization (i.e., removal of cells and/or cellular components).

Finally, other assays that identify cell-specific components (e.g., surface antigens) can be used to determine if the tissue matrices are acellular.

In general, the steps involved in the production of an acellular tissue matrix include harvesting the tissue from a donor (e.g., a human cadaver or animal source) and cell removal under conditions that preserve biological and structural function. In certain embodiments, the process includes chemical treatment to stabilize the tissue and avoid biochemical and structural degradation together with or before cell removal. In various embodiments, the stabilizing solution arrests and prevents osmotic, hypoxic, autolytic, and proteolytic degradation, protects against microbial contamination, and reduces mechanical damage that can occur with tissues that contain, for example, smooth muscle components (e.g., blood vessels). The stabilizing solution may contain an appropriate buffer, one or more antioxidants, one or more oncotic agents, one or more antibiotics, one or more protease inhibitors, and/or one or more smooth muscle relaxants.

The tissue is then placed in a decellularization solution to remove viable cells (e.g., epithelial cells, endothelial cells, smooth muscle cells, and fibroblasts) from the structural matrix without damaging the biological and structural integrity of the collagen matrix. The decellularization solution may contain an appropriate buffer, salt, an antibiotic, one or more detergents (e.g., TRITON X-100™, sodium deoxycholate, polyoxyethylene (20) sorbitan mono-oleate), one or more agents to prevent cross-linking, one or more protease inhibitors, and/or one or more enzymes. In some embodiments, the decellularization solution comprises 1% TRITON X-100™ in RPMI media with Gentamicin and 25 mM EDTA (ethylenediaminetetraacetic acid). In some embodiments, the tissue is incubated in the decellularization solution overnight at 37° C. with gentle shaking at 90 rpm. In certain embodiments, additional detergents may be used to remove fat from the tissue sample. For example, in some embodiments, 2% sodium deoxycholate is added to the decellularization solution.

After the decellularization process, the tissue sample is washed thoroughly with saline. In some exemplary embodiments, e.g., when xenogenic material is used, the decellularized tissue is then treated overnight at room temperature with a deoxyribonuclease (DNase) solution. In some embodiments, the tissue sample is treated with a DNase solution prepared in DNase buffer (20 mM HEPES (4-(2-hydroxyethyl)-1-piperazineethanesulfonic acid), 20 mM $CaCl_2$ and 20 mM $MgCl_2$). Optionally, an antibiotic solution (e.g., Gentamicin) may be added to the DNase solution. Any suitable buffer can be used as long as the buffer provides suitable DNase activity.

While an acellular tissue matrix may be made from one or more individuals of the same species as the recipient of the acellular tissue matrix graft, this is not necessarily the case. Thus, for example, an acellular tissue matrix may be made from porcine tissue and implanted in a human patient. Species that can serve as recipients of acellular tissue matrix and donors of tissues or organs for the production of the acellular tissue matrix include, without limitation, mammals, such as humans, nonhuman primates (e.g., monkeys, baboons, or chimpanzees), pigs, cows, horses, goats, sheep, dogs, cats, rabbits, guinea pigs, gerbils, hamsters, rats, or mice.

Elimination of the α-gal epitopes from the collagen-containing material may diminish the immune response against the collagen-containing material. The α-gal epitope is expressed in non-primate mammals and in New World monkeys (monkeys of South America) as well as on macromolecules such as proteoglycans of the extracellular components. U. Galili et al., J. Biol. Chem. 263: 17755 (1988). This epitope is absent in Old World primates (monkeys of Asia and Africa and apes) and humans, however. Id. Anti-gal antibodies are produced in humans and primates as a result of an immune response to α-gal epitope carbohydrate structures on gastrointestinal bacteria. U. Galili et al., Infect. Immun. 56: 1730 (1988); R. M. Hamadeh et al., J. Clin. Invest. 89: 1223 (1992).

Since non-primate mammals (e.g., pigs) produce α-gal epitopes, xenotransplantation of collagen-containing material from these mammals into primates often results in rejection because of primate anti-Gal binding to these epitopes on the collagen-containing material. The binding results in the destruction of the collagen-containing material by complement fixation and by antibody dependent cell cytotoxicity. U. Galili et al., Immunology Today 14: 480 (1993); M. Sandrin et al., Proc. Natl. Acad. Sci. USA 90: 11391 (1993); H. Good et al., Transplant. Proc. 24: 559 (1992); B. H. Collins et al., J. Immunol. 154: 5500 (1995). Furthermore, xenotransplantation results in major activation of the immune system to produce increased amounts of high affinity anti-gal antibodies. Accordingly, in some embodiments, when animals that produce α-gal epitopes are used as the tissue source, the substantial elimination of α-gal epitopes from cells and from extracellular components of the collagen-containing material, and the prevention of re-expression of cellular α-gal epitopes can diminish the immune response against the collagen-containing material associated with anti-gal antibody binding to α-gal epitopes.

To remove α-gal epitopes, after washing the tissue thoroughly with saline to remove the DNase solution, the tissue sample may be subjected to one or more enzymatic treatments to remove certain immunogenic antigens, if present in the sample. In some embodiments, the tissue sample may be treated with an α-galactosidase enzyme to eliminate α-gal epitopes if present in the tissue. In some embodiments, the tissue sample is treated with α-galactosidase at a concentration of 300 U/L prepared in 100 mM phosphate buffer at pH 6.0. In other embodiments, the concentration of α-galactosidase is increased to 400 U/L for adequate removal of the α-gal epitopes from the harvested tissue. Any suitable enzyme concentration and buffer can be used as long as sufficient removal of antigens is achieved.

Alternatively, rather than treating the tissue with enzymes, animals that have been genetically modified to lack one or more antigenic epitopes may be selected as the tissue source. For example, animals (e.g., pigs) that have been genetically engineered to lack the terminal α-galactose moiety can be selected as the tissue source. For descriptions of appropriate animals see co-pending U.S. application Ser. No. 10/896,594 and U.S. Pat. No. 6,166,288, the disclosures of which are incorporated herein by reference in their entirety. In addition, certain exemplary methods of processing tissues to produce acellular matrices with or without reduced amounts of or lacking alpha-1,3-galactose moieties, are described in Xu, Hui. et al., "A Porcine-Derived Acellular Dermal Scaffold that Supports Soft Tissue Regeneration: Removal of Terminal Galactose-α-(1,3)-Galactose and Retention of Matrix Structure," Tissue Engineering, Vol. 15, 1-13 (2009), which is incorporated by reference in its entirety.

After the acellular tissue matrix is formed, histocompatible, viable cells may optionally be seeded in the acellular tissue matrix to produce a graft that may be further remodeled by the host. In some embodiments, histocompatible viable cells may be added to the matrices by standard in vitro cell co-culturing techniques prior to transplantation, or by in vivo repopulation following transplantation. In vivo repopulation can be by the recipient's own cells migrating into the acellular tissue matrix or by infusing or injecting cells obtained from the recipient or histocompatible cells from another donor into the acellular tissue matrix in situ. Various cell types can be used, including embryonic stem cells, adult stem cells (e.g. mesenchymal stem cells), and/or neuronal cells. In various embodiments, the cells can be directly applied to the inner portion of the acellular tissue matrix just before or after implantation. In certain embodiments, the cells can be placed within the acellular tissue matrix to be implanted, and cultured prior to implantation.

What is claimed is:

1. A method for producing a tissue composition, comprising:
    selecting a tissue matrix;
    treating the tissue matrix to produce fragments having a length between about 5 μm and 300 μm;
    forming the fragments into a plurality of flowable particles, each particle having a longest dimension between about 1 mm and about 5 mm; and
    drying the particles.

2. The method of claim 1, wherein drying the particles includes subjecting the particles to a convective drying process.

3. The method of claim 1, further including treating the particles with a dehydrothermal treatment process.

4. The method of claim 1, wherein forming the fragments into a plurality of particles includes compressing groups of the fragments to produce each particle.

5. The method of claim 1, wherein forming the fragments into a plurality of particles includes placing small groups of the fragments in a cold environment to freeze the groups.

6. The method of claim 5, wherein placing small groups of the fragments in a cold environment to freeze the groups includes extruding the small groups into a cryogenic liquid.

7. The method of claim 1, wherein the plurality of particles includes substantially spherical particles.

8. The method of claim 1, wherein treating the tissue matrix to produce fragments includes milling the tissue matrix.

9. The method of claim 1, wherein the fragments are strands of tissue matrix.

10. The method of claim 1, wherein the tissue matrix is dermal tissue matrix.

11. The method of claim 1, wherein the tissue matrix is porcine tissue matrix.

12. The method of claim 1, wherein the tissue matrix is an acellular tissue matrix.

* * * * *